US011475400B2

(12) United States Patent
Johnson et al.

(10) Patent No.: US 11,475,400 B2
(45) Date of Patent: Oct. 18, 2022

(54) LOW-POWER SIGNALING FOR MEDICAL DEVICES AND MEDICAL DEVICE PERSONNEL

(71) Applicant: ZOLL Medical Corporation, Chelmsford, MA (US)

(72) Inventors: Guy Robert Johnson, Gloucester, MA (US); Gary A. Freeman, Waltham, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 16/502,952

(22) Filed: Jul. 3, 2019

(65) Prior Publication Data

US 2019/0325380 A1 Oct. 24, 2019

Related U.S. Application Data

(63) Continuation of application No. 15/854,954, filed on Dec. 27, 2017, now Pat. No. 10,387,830, which is a continuation of application No. 15/076,085, filed on Mar. 21, 2016, now Pat. No. 9,886,680.

(60) Provisional application No. 62/137,753, filed on Mar. 24, 2015.

(51) Int. Cl.
*G06Q 10/08* (2012.01)
*A61N 1/39* (2006.01)

(52) U.S. Cl.
CPC ......... *G06Q 10/087* (2013.01); *A61N 1/3904* (2017.08); *A61N 1/3993* (2013.01)

(58) Field of Classification Search
CPC ...... A61N 1/39; A61N 1/3904; A61N 1/3993; G06Q 10/087
See application file for complete search history.

(56) References Cited

U.S. PATENT DOCUMENTS

| 9,740,746 | B2* | 8/2017 | Clifford ............ G06F 16/24575 |
| 9,886,680 | B2 | 2/2018 | Johnson et al. |
| 2003/0088275 | A1* | 5/2003 | Palmer ..................... A61N 1/37 607/5 |
| 2004/0024644 | A1 | 2/2004 | Gui et al. |
| 2008/0103941 | A1* | 5/2008 | Hussain ............... G06Q 10/087 705/28 |
| 2009/0124303 | A1 | 5/2009 | Twitchell, Jr. |
| 2010/0187306 | A1 | 7/2010 | Solomon |
| 2013/0262241 | A1 | 10/2013 | Nelson |

(Continued)

OTHER PUBLICATIONS

Adler A, Halkin A, Viskin S. Wearable Cardioverter-Defibrillators. Circulation. vo. 127. Issue 7. 2013. 854-860. doi: 10.1161. cir.112. 146530 (Year: 2013).*

(Continued)

*Primary Examiner* — Nader Bolourchi
(74) *Attorney, Agent, or Firm* — Finch & Maloney PLLC (57) ABSTRACT

Aspects of the present disclosure are directed toward apparatuses, systems, and methods that include at least one medical device having a device transceiver configured to wirelessly broadcast a device signal including at least unique identifier data and an information system is configured to maintain an active list of medical device inventory associated with a particular emergency response vehicle, and the processor is configured to automatically determine presence of the at least one medical device.

28 Claims, 3 Drawing Sheets

(56) References Cited

U.S. PATENT DOCUMENTS

2014/0025131 A1* 1/2014 Sullivan .............. A61N 1/3993
607/5
2015/0109125 A1* 4/2015 Kaib ................... A61N 1/3993
340/539.12
2015/0220296 A1 8/2015 Lin

OTHER PUBLICATIONS

Jiuqiang Xu, et al., "Distance Measurement Model Based on RSSI in WSN,"Wireless Sensor Network, 2010, 2, 606-611, Scientific Research, doi:10.4236/wsn.2010.28072 Published Online Aug. 2010 (http://ww.sciRp.org/journal/wsn).
"Getting Started with iBeacon,", version 1.0, Apple, Jun. 2, 2014, (11 pgs.).
"Specification of the Bluetooth System, Master Table of Contents & Compliance Requirements,", Covered Core Package Version 4.0, Jun. 30, 2010, vols. 1-6, Bluetooth SIG, (2302 pgs.).
"Specification of the Bluetooth System, Master Table of Contents & Compliance Requirements,", Covered Core Package Version 4.1, Dec. 3, 2013, vols. 1-7, Bluetooth SIG, (2684 pgs.).

* cited by examiner

LOW-POWER SIGNALING FOR MEDICAL DEVICES AND MEDICAL DEVICE PERSONNEL

CROSS-REFERENCE TO RELATED APPLICATIONS

This application is a continuation of prior application Ser. No. 15/854,954, filed on Dec. 27, 2017, entitled "Low-Power Signaling For Medical Devices and Medical Device Personnel," which is a continuation of prior application Ser. No. 15/076,085, filed on Mar. 21, 2016, entitled "Low-Power Signaling For Medical Devices and Medical Device Personnel," which claims the benefit of U.S. Provisional Patent Application Ser. 62/137,753, filed on Mar. 24, 2015, entitled "Low-Power Signaling For Medical Devices and Medical Device Personnel," each of which is incorporated herein by reference in their entirety for all purposes.

TECHNICAL FIELD

The present invention relates to systems and methods for determining the location of one or more medical devices. More specifically, the present invention relates to systems and methods for determining a presence or location of multiple medical devices, and presenting the information regarding the presence of the medical devices on a user interface.

BACKGROUND

Medical devices used in emergency medical service (EMS) applications or emergency response situations, for example, defibrillators, are typically complex and expensive. The presence and/or locations of such devices are typically tracked and inventoried manually (for example, verbally or via an electronic log). Thus, it may be cumbersome to efficiently track and locate medical devices in certain situations, such as mass casualty situations.

Further, medical devices can include wireless data transceivers to transmit medical information for storage in a remote medical database. However, some designs lack relatively long-range communication components (such as cellular or Wi-Fi transceivers) and in some situations, such as mass casualty situations, relatively long-range communication methods may be unavailable. In these cases, some medical devices may turn to relatively short-range, device-to-device communication methods (such as near-field communications (NFC), Bluetooth, and the like) to transmit information.

SUMMARY

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical device inventory associated with a particular emergency response vehicle, and the processor is configured to automatically determine presence of the at least one medical device in response to the system transceiver receiving the device signal, and provide an indication on the at least one display device if the at least one medical device is present.

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical device inventory associated with a particular emergency response vehicle, and the processor is configured to automatically determine presence of the at least one medical device in response to the system transceiver receiving the device signal, measure a signal strength of the device signal and determine whether the at least one medical device is in one of at least three location-based conditions in response thereto, and provide an indication on the at least one display device if the at least one medical device is present and the location-based condition of the at least one medical device.

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical devices associated with a particular emergency response situation, and the processor is configured to automatically determine presence of the at least one medical device in response to the system transceiver receiving the device signal, and provide an indication on the at least one display device if the at least one medical device is present.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
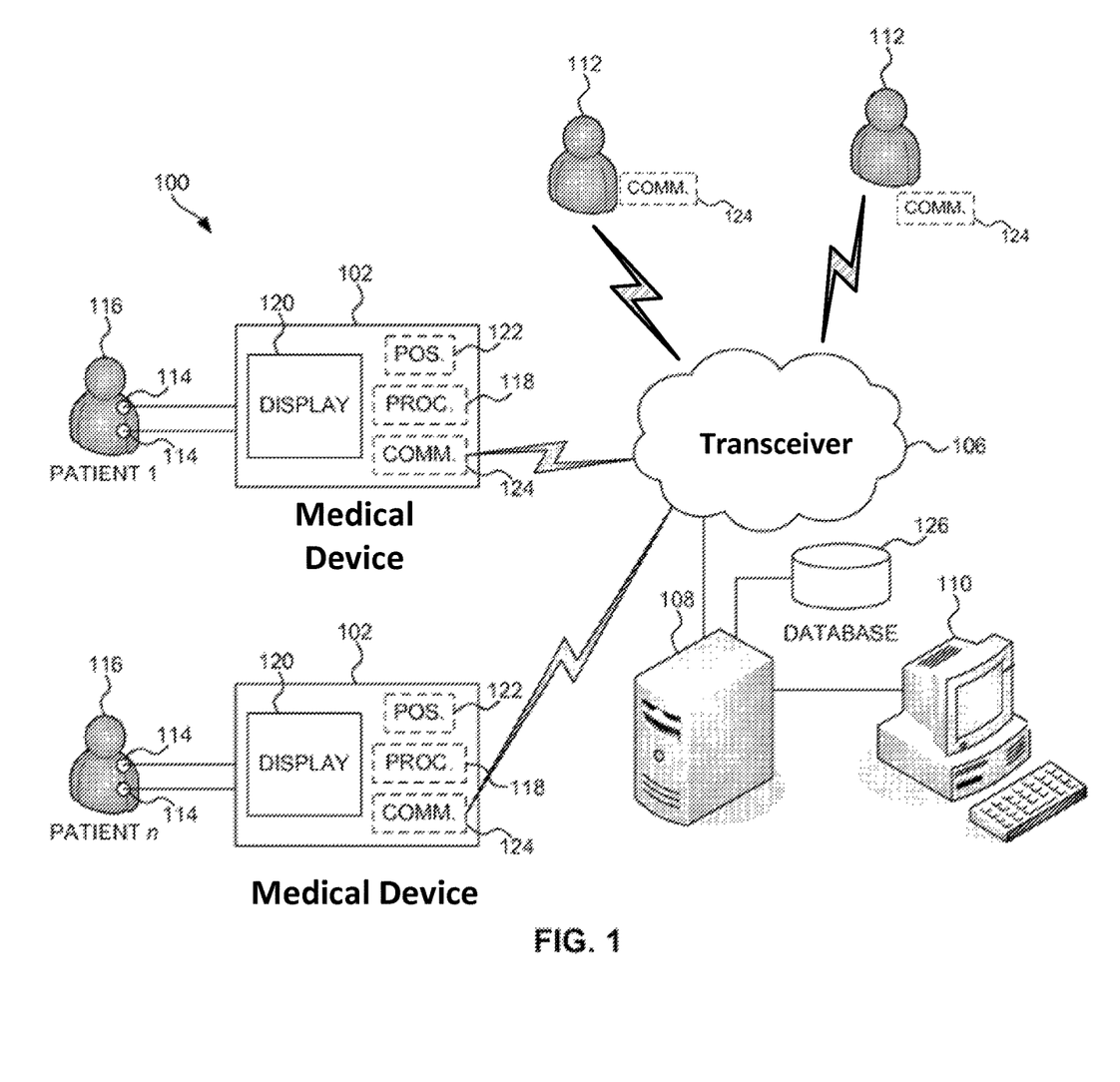
FIG. 1 illustrates a system for determining the presence of one or more medical devices, consistent with various aspects of the present disclosure.

FIG. 1 illustrates a system 100 for determining the presence of one or more medical devices 102. The medical devices 102 can be used in connection with a particular emergency response vehicle or a particular emergency response situation. The medical devices 102 wirelessly transmit and communicate data using, for example, low-power Bluetooth, near-field communications (NFC), WiFi, cellular, ZigBee radio, and the like, to an information system 108 (e.g., hand-held device, tablet, smart phone, laptop computer, desktop computer) via a system transceiver 106. The medical devices 102 can receive signals from one or more sensors or electrodes 114 coupled to the patient 116. In some embodiments, a processor 118 uses such signals to monitor, detect, and/or derive or calculate various patient conditions. For example, the processor 118 may monitor, detect, and/or derive or calculate heart rate, blood pressure, temperature, respiration rate, blood oxygen level, end-tidal carbon dioxide level, pulmonary function, blood glucose level, and/or weight. In some embodiments, the medical device 102 includes a display 120 for presenting data associated with one or more of the above medical parameters. For example, the display 120 may present an electrocardiograph (ECG).

The medical devices 102 may be, for example, defibrillators (such as ZOLL® X-Series® or E-Series® devices), automatic external defibrillators (AEDs, such as ZOLL® AED Pro® devices), wearable cardioverter defibrillators (such as ZOLL® LifeVest® devices), combinations thereof, and the like. Some of the medical devices 102 may be assigned to patients (that is, currently connected to patients and gathering data), and some of the medical devices 102 may be unassigned (that is, currently disconnected from patients and not gathering data). For simplicity, the following paragraphs only provide the details for one assigned medical device 102. It is to be understood, however, that in some embodiments similar details apply to each of the different types of devices 102.

The medical device 102 receives signals from one or more sensors or electrodes 114 coupled to the patient 116. In some embodiments, a processor 118 uses such signals to monitor, detect, and/or derive or calculate various patient conditions. For example, the processor 118 may monitor, detect, and/or derive or calculate heart rate, blood pressure, temperature, respiration rate, blood oxygen level, end-tidal carbon dioxide level, pulmonary function, blood glucose level, and/or weight. In some embodiments, the medical device 102 includes a display 120 for presenting data associated with one or more of the above medical parameters. For example, the display 120 may present an electrocardiograph (ECG).

A transceiver 124 is provided with each of the medical devices 102 to wirelessly transmit and communicate a device signal that includes the above noted data. The transceiver 124 can be provided integrally with the medical devices 102, or the transceiver 124 may be removable. The device signal can include a short message having a universally unique identified (UUID), that is associated with a given one of the medical devices 102, a Major Identifier, Minor Indenter and/or data indicative of a power (signal strength) calibration value. The calibration value is a stored value that indicates specific distances the transceiver 124 is away from the information system 108 based on the power or signal strength. This calibration value can be provided by measuring various distances (one foot, two feet, three feet) the transceiver 124 is away from the information system 108, noting the power or signal strength at those points, and storing the association between the power or signal strength value and the various distances. In this manner, the spacial location of the transceiver 124 can be determined with respect to its distance from the information system 108. The transceiver 124, when associated with the medical devices 102, is referred to as a device transceiver. Further, in embodiments where the transceiver 124 is provided as part of a device, the processor of the medical device 102 is configured to wirelessly broadcast the device signal on a regular basis. The device signal can also include stored device information (for example, the device's type, model number, serial number, device capabilities, assigned setting, such as an ambulance or hospital, and the like) and/or associated patient information (that is, information about the patient 116 to which the medical device 102 is assigned) to the information system 108 via the system transceiver 106. Such patient information may include, for example, the patient's name, age, weight, height, medical history, past and/or real-time medical data obtained by the medical device 102, and the like. In some embodiments, the system 100 may use the ZOLL® RescueNet® Link system to transmit medical data obtained by the medical devices 102 to the information system 108.

The UUID can be a 16 byte string used to differentiate a large group of related medical devices 102. For example, all Automatic External Defibrillators from the same manufacturer would use the same UUID. This allows the information system 108 identify the medical devices 102 used to identify AED's. The major identifier can be a 2 byte string used to distinguish a subset of medical devices 102 within the larger group. The minor identifier can be a 2 byte string meant to identify an individual medical device 102. The data indicative of a power can be used to determine a proximity (distance) the medical device 102 is from the information system 108. The data indicative of power is defined as the strength of the signal a known distance (for example, a meter, two meters, or three meters) between the medical device 102 and the information system 108. This value is recorded, and the information system 108 uses this power as a baseline to give a rough distance estimate.

In certain embodiments, as discussed in further detail below, a transceiver 124, consistent with various aspects of the present disclosure, can be provided with a medical device personnel 112 (or crew member) and wirelessly broadcast a crew signal to the information system 108. In these embodiments, the transceiver 124 may be a standalone device, or can be provided as part of, for example, a smart watch, smart phone, or tablet that is carried by or on the medical device personnel 112. Further, in embodiments where the transceiver 124 is provided as part of a device, the device's processor is configured to wirelessly broadcast the crew signal on a regular basis. In instances where the transceiver 124 is provided as a standalone device, the standalone device also includes a processor that is configured to wirelessly broadcast the crew signal on a regular basis. Similar to the medical devices 102, the transceiver 124 provided with the medical device personnel 112 carries the crew signal with a short message having a universally unique identified (UUID), that is associated with the medical device personnel 112, a Major Identifier, Minor Indenter and/or data indicative of a power (signal strength) calibration value. The calibration value is a stored value that indicates specific distances the transceiver 124 is away from the information system 108 based on the power or signal strength. This calibration value can be provided by measuring various distances (one foot, two feet, three feet) the transceiver 124 is away from the information system 108, noting the power or signal strength at those points, and storing the association between the power or signal strength value and the various distances. In this manner, the spacial location of the transceiver 124 can be determined with respect to its distance from the information system 108. The transceiver 124, when associated with the medical device personnel 112, is referred to as a mobile transceiver.

A database 126 in communication with the information system 108 stores device information (for example, device types, model numbers, serial numbers, device capabilities, assigned setting, and the like). More specifically, the database 126 stores information that includes an active list of medical device inventory associated with the particular emergency response vehicle or particular emergency response situation. The information system 108 associates the data wirelessly transmitted by one or more of the medical devices 102 with information about one or more of the medical devices 102 that is stored in the database 126. Similarly, in some embodiments the database 126 (or another database) stores information about one or more medical device personnel 112. The information system 108 associates the data wirelessly transmitted by the transceiver 124 associated with one or more medical device personnel 112 with information about one or more medical device personnel 112 that is stored in the database 126. In addition, the database 126 can store data related to a storage capacity of an emergency response vehicle, and data indicative of a storage location of the active list of medical device inventory within the emergency response vehicle.

In response to the system transceiver 106 receiving the device signal (or crew signal), the information system 108 automatically determines the presence of the medical devices 102. In certain embodiments, the information system 108 measures a signal strength of the device signal (or crew signal), and determines whether the associated medical device 102 is in one of at least three location-based conditions. In addition, the information system 108 provides an indication on the at least one display device 110 if the medical device 102 is present. In embodiments where the location-based condition is measured, the information system 108 also provides an indication of the location-based condition on the display device 110. The data wirelessly transmitted from one of the medical devices 102 is unique to that device. Thus, the information system 108 is configured to automatically determine the presence of more than one of the medical devices 102 in response to receiving the associated the device signal. In these instances, the information system 108 provides an indication on the display device 110 if the information system 108 senses that the medical device 102 is present. In certain embodiments, the information system 108 is configured to scan for known transceivers 124. In addition, if the transceiver 124 is sensed, the information system 108 logs the contact event in the database 126.

As noted above, the information system 108 is configured to automatically determine the presence of more than one medical device 102 and/or more than one medical device personnel 112 based in response to the system transceiver 106 receiving an associated device signal or crew signal. In these instances, the information system 108 is configured to provide an indication on the at least one display device 110 if the one or more of the medical devices 102 and/or medical device personnel 112 are present. More specifically, the display device 110 displays data indicative of each medical devices 102 and/or each medical device personnel 112 if the information system 108 senses the associated device signal or crew signal.

The embodiments discussed herein may also be considered as methods as operated and/or executing by the system discussed consistent with various aspects of the present disclosure.

Figure 2:
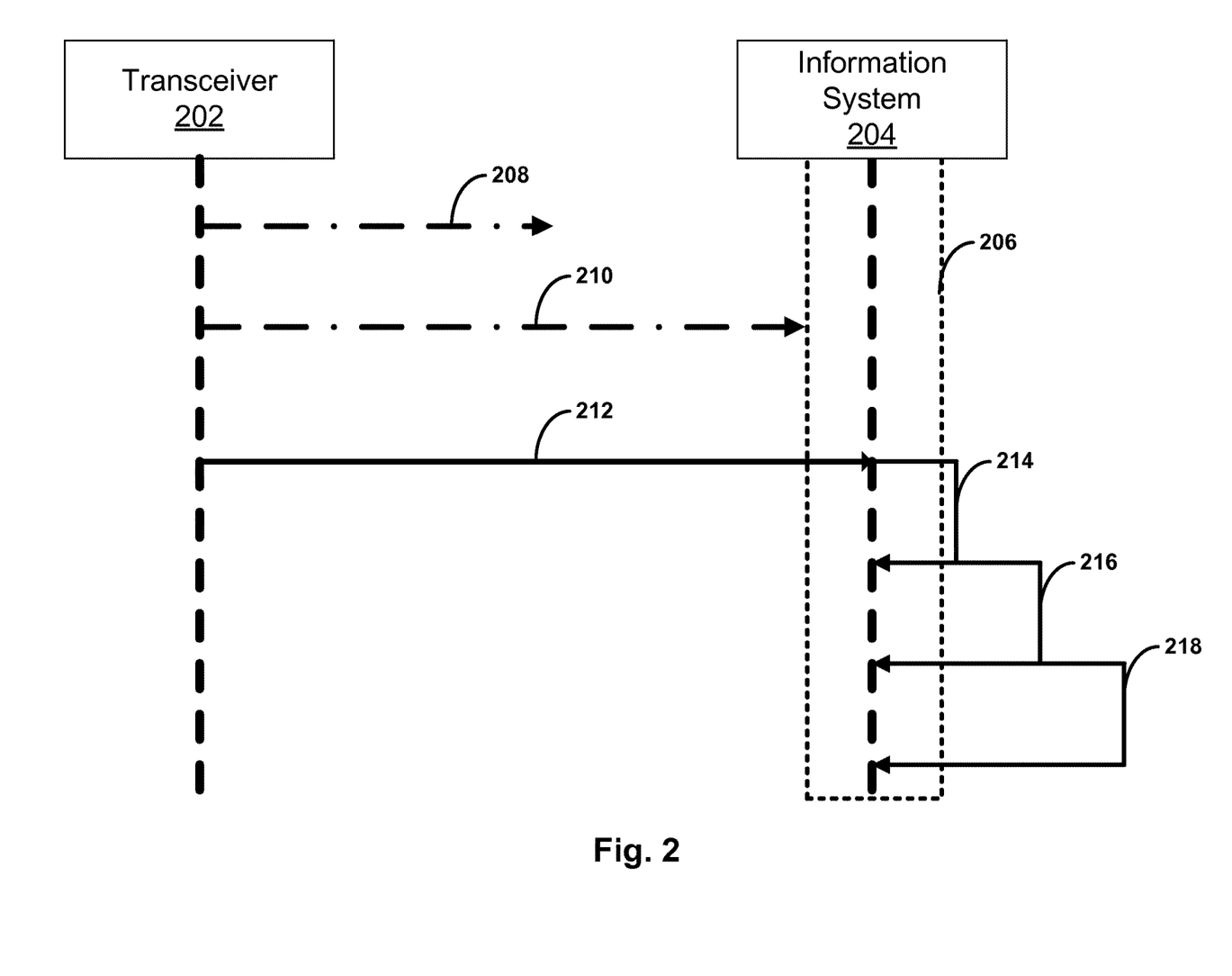
FIG. 2 illustrates an example communication and detection of a transceiver carried with a medical device or by a medical device personnel, consistent with various aspects of the present disclosure.

FIG. 2 illustrates an example communication and detection of a transceiver 202 carried with a medical device or by a medical device personnel, consistent with various aspects of the present disclosure. As noted above in connection with FIG. 1, the transceiver 202 communicates a data signal (208/210/212) that is detected by an information system 204. The information system 204 (system transceiver not shown) has a range 206 in which the data signal (208/210/212) is sensed. For instance, the data signal (208/210/212) is shown in three different strengths. The first strength 208 lies outside the range 206 of the information system 204, the second strength 210 touches or is adjacent to the range 206 of the information system 204, and the third signal strength 212 is within the range 200 of the information system 204. In instances where the transceiver 202 communicates at the first strength 208, the presence of the transceiver 202 (and its associated medical device or medical device personnel) will not be sensed by the information system 204 as the transceiver 202 is out of range 206 of the information system 204. In instances where the transceiver 202 communicates at the second strength 210, the presence of the transceiver 202 (and its associated medical device or medical device personnel) is sensed by the information system 204, but the data/information carried by the transceiver 202 is not within the range 206 of the information system 204 such that the data/information can be read and/or stored by the information system 204. In instances where the transceiver 202 communicates at the third strength 212, the presence of the transceiver 202 (and its associated medical device or medical device personnel) is sensed by the information system 204, and the data/information carried by the transceiver 202 can be read and/or stored by the information system 204.

In response to the information system 204 sensing the presence of the transceiver 202 communicating at the third strength 212, the data/information carried by the transceiver 202 can be read 214 by the information system 204 against a database stored therein. As noted above, the information system 204 can include a database that stores an active list of medical device inventory associated with an emergency response vehicle or emergency response situation. In other embodiments, the information system 204 can include a second database that stores an active list of medical device personnel associated with an emergency response vehicle or emergency response situation. The information system 204 also logs 216 that the data/information carried by the transceiver 202 has been read 214 by the information system 204. This allows for the information system 204 to track which medical devices or medical device personnel are present. Further, the information system 204 also provides an alert on 218 (on a user interface) indicating presence of one or more medical devices and/or medical device personnel in response to sensing the presence of the transceiver 202 associated with one or more medical devices or medical device personnel. Further, the information system 108 can indicate, on the display 110, the inventory information, which can be verified by a user (such as a crew member for the emergency response vehicle or emergency response situation), who can verify that all medical devices 102 are reloaded before leaving a scene.

In certain embodiments, based on sensing the relative strength of the data signal (208/210/212), such as the device signal or crew signal, broadcast by the transceiver 202, the information system 204 can automatically determine a spatial location of the transceiver 202 and its associated medical device or medical device personnel. In addition, the information system 204 (via its processor) can provide an alert on a display device indicating that the associated medical device or medical device personnel is present. Further, the information system 204 provides an indication that the medical device or medical device personnel is missing in response to the data signal (208/210/212), such as the device signal or crew signal, being out of range of the information system 204.

In certain embodiments, the information system 204 is configured to measure a signal strength of the data signal (208/210/212), such as a device signal or crew signal, as broadcast by the transceiver 202 and its associated medical device or medical device personnel. In these embodiments, the information system 204 determines whether the at least one medical device or medical device personnel is in one of at least three location-based conditions in response thereto. As noted above, the data signal (208/210/212) indicates whether the transceiver 202 lies outside the range 206 of the information system 204 (first strength 208), the transceiver touches or is adjacent to the range 206 of the information system 204 (second strength 210), or the transceiver 202 is within the range 206 of the information system 204 (third signal strength 212). In such an embodiment, the information system 204 provides an indication on its display device if the at least one medical device or medical device personnel is present, and the location-based condition of the at least one medical device or medical device personnel. The display can provide the location-based condition indicating as whether the transceiver 202 lies outside the range 206 of the information system 204 (first strength 208), the transceiver 202 is in a pairing condition (third signal strength 212), or whether the transceiver 202 can be sensed, but is not close enough to be paired (e.g., an intermediate condition).

Figure 3:
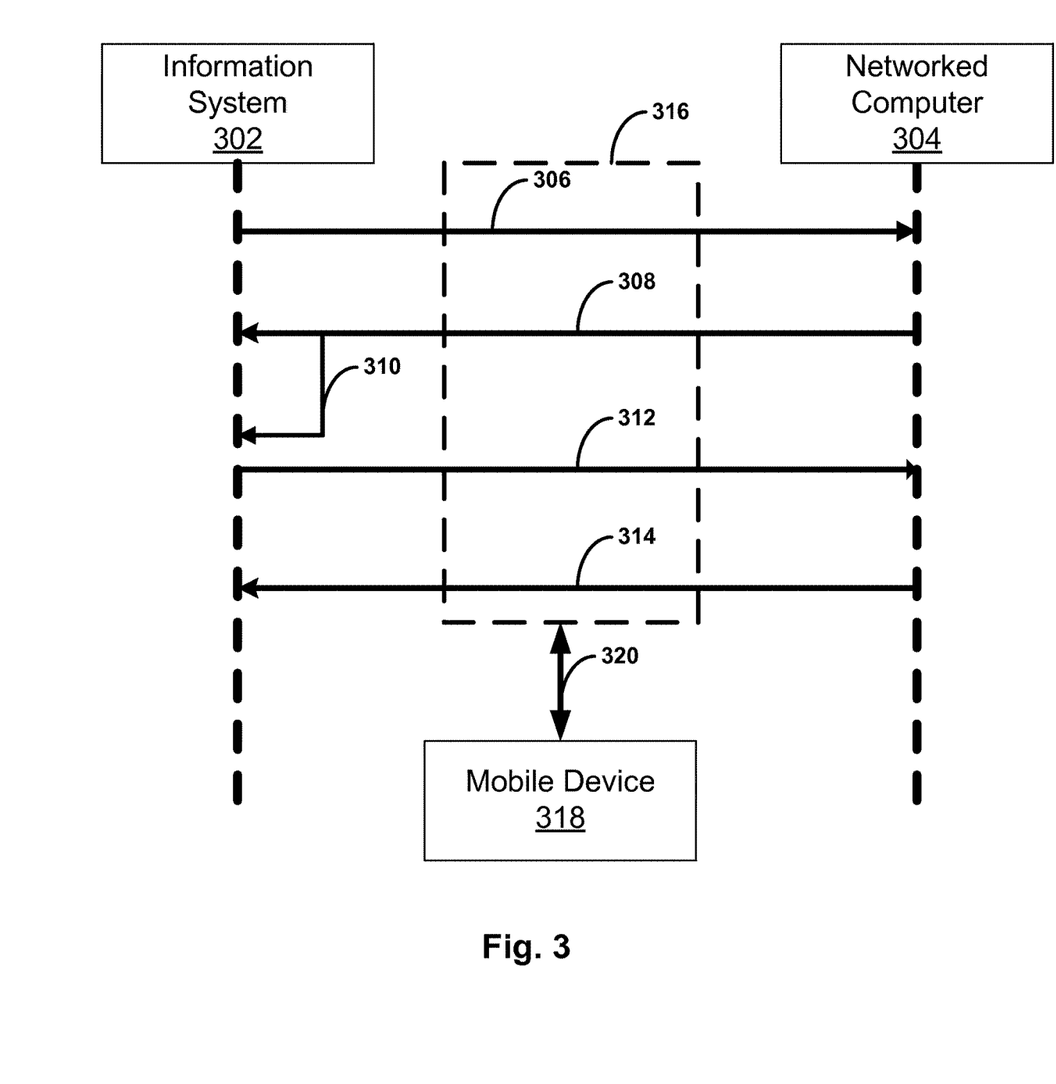
FIG. 3 illustrates an example communication between an information system and a networked computer, consistent with various aspects of the present disclosure.

FIG. 3 illustrates an example communication between an information system 302 and a networked computer 304, consistent with various aspects of the present disclosure. As discussed above, the information system 302 is configured to communicate with one or medical devices and/or medical device beacons based on receiving low-power signals broadcast by a transceiver. The information system 302, in certain embodiments, can also wirelessly communicate with the networked computer 304 in order to exchange data, or offload data for detailed computations. For instance, the information system 302 can include an internal database, as described above, and the networked computer 304 can also include a database. Each database can store data indicative of a storage capacity of an emergency response vehicle (or emergency response situation), and data indicative of a storage location of the active list of medical device inventory within the emergency response vehicle (or emergency response situation).

In certain embodiments, the information system 302 wirelessly communicates 306 a current active inventory list of medical devices or medical device personnel to the networked computer 304. The networked computer 304 can, as prompted by the information system 302 or a user at the networked computer 304, communicate 308 an updated inventory list of medical devices or medical device personnel to the information system 302. The information system 302 will compare 310 the current active inventory list of medical devices or medical device personnel to the list transmitted by the networked computer 304, and update the active list of inventory as necessary. The information system 302 can then communicate the changes in inventory back 312 to the networked computer 304. Further, the networked computer 304 can communicate an acknowledgement 314 that the information system 302 has the correct inventory of medical devices or medical device personnel stored thereon.

In certain embodiments, the information system 302 and the networked computer 304 communicate via a cloud-based server 316. In these embodiments, the cloud-based server 316 can also include a database that stores the communicated messages, and related inventory information. The cloud-based server 316 can enable communication 320 with at least one mobile device 318. In addition, the cloud-based server 316 can enable communication with other devices or computers. Further, the cloud-based server 316 allows for communication of inventory information across multiple systems. For instance, medical devices may be part of the same inventory that is accessed by more than one information system 302. As a result, the inventory can be tracked based on which information system 302 is using, a certain medical device. Further, more than one networked computer 304 may be provided. Each networked computer 304 may communicate with another networked computer 304 using peer-to-peer networking.

In certain embodiments, the networked computer 304 may monitor the information collected by the information system 302, as described in detail above. In this manner, the networked computer 304 may communicate with another networked computer 304 and transfer monitoring responsibilities therebetween.

As noted above, in certain embodiments, the cloud-based server 316 can be accessed by at least one mobile device 318. The mobile device 318 can include various mobile applications that interact with the information system 302. For instance, the cloud-based server 316 can store the data collected by the information system 302, and a mobile application run by the mobile device 318 queries the cloud-based server 316 with information regarding a specific medical device or medical device personnel (equipped with the above noted transceiver). In this manner, the mobile device 318 is able to confirm the location of the specific medical device or medical device personnel, the status of the specific medical device or medical device personnel, or other related information. Further, a user of the mobile device 318 can add a picture of the GPS location or inventory location of a medical device or medical device personnel, which can be communicated to the cloud-based server 316. The cloud-based server 316 can then associate this picture data with the associated medical device or medical device personnel. Such location-based GPS information can also be associated, by the mobile device 318, with other travel service applications (e.g. WAZE, GARMIN) or other beacon-type applications.

The mobile application provided with the mobile device 318 can incorporate other applications. For instance, the mobile application can provide CPR instruction, CPR compression depth and rate when possible if the networked medical device, communicating through the cloud-based server, includes the interactive capabilities (e.g., an AED equipped with CPR data capabilities). Further, the mobile application can automatically communicate with a medical device, to obtain treatment data. The mobile application can upload this data to the cloud-based server 316, which can be relayed to an EMS service or medical device personnel. The mobile application can incorporate other modules to assess patient; e.g. use microphone to analyze heart sound or breathing sounds.

The cloud-based server 316 can also provide the mobile device 318 with access to the system via an installer mobile application that allows the mobile device 318 to be trusted/verified. The mobile device 318 can then receive information regarding various medical devices such as the device location model, manufacturer, battery type, service interval, contact information, and EMS contact information. The mobile application can also query the cloud-based server 316 in information mode and location information will be provided. Further, in an emergency response situation, a mobile application can query the cloud-based server 316 in emergency mode signaling a medical emergency. During a medical emergency the cloud-based server 316 can notify other mobile application users of the medical emergency and the need for a particular medical device (such as an AED). Responding mobile app users will be supplied with location and navigation information to retrieve the closest AED and transport it to the user making the request. More than one user can be notified to locate and transport an AED to the user reporting the medical emergency.

In certain embodiments, the cloud-based server 316 can notify a mobile application user of possible maintenance need and readiness check when a medical device is requested. When available server will periodically query the medical device via the cloud-based server 316 for readiness status and update records as needed. Thus, the cloud-based server 316 tracks possible need for medical device service. In this manner, when the medical device has been serviced, a user having the mobile application can update the cloud-based server 316. Further, if a medical device is requested and closest medical device has outstanding service need associated with it, the cloud-based server 316 can provide alternate locations.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device system, comprising:
   a transceiver;
   a display device; and
   at least one processor coupled with the transceiver and the display device, the at least one processor being configured to:
   sense a presence of a first defibrillator within a range of the transceiver based on the transceiver receiving a first device signal generated by the first defibrillator, the first device signal having a first signal strength;
   receive a second device signal from a second defibrillator via the transceiver;
   measure a second signal strength of the second device signal;
   estimate a first distance between the first defibrillator and the transceiver based on the first signal strength;
   estimate a second distance between the second defibrillator and the transceiver based on the second signal strength;
   maintain an active list of medical device inventory, the active list comprising information regarding a first storage location of the first defibrillator, the first distance, a second storage location of the second defibrillator, and the second distance;
   provide an indication of the estimated first distance between the first defibrillator and the transceiver and an indication of the estimated second distance between the second defibrillator and the transceiver via the display device; and
   provide an alert via the display device in response to sensing the presence of the first defibrillator within the range of the transceiver.

2. The medical device system of claim 1, wherein one or both of the first device signal and the second device signal comprises stored device information that includes one or more of type, model number, serial number, or capabilities of the first defibrillator and the second defibrillator.

3. The medical device system of claim 1, wherein one or both of the first device signal and the second device signal comprises associated patient information that includes one or more of a patient's name, age, weight, or medical history.

4. The medical device system of claim 1, wherein the first storage location of the first defibrillator and/or the second storage location of the second defibrillator are within an emergency response vehicle.

5. The medical device system of claim 1, wherein the at least one processor is further configured to provide the indication of the first distance and the second distance to a mobile device in response to a request received from the mobile device.

6. The medical device system of claim 5, wherein the at least one processor is further configured to provide navigation information associated with the first defibrillator and/or the second defibrillator to the mobile device.

7. The medical device system of claim 1, wherein the indication of the estimated first distance includes a first location-based condition of the first defibrillator and the indication of the estimated second distance includes a second location-based condition of the second defibrillator.

8. The medical device system of claim 1, wherein the at least one processor is further configured to provide data indicative of a location of the display device.

9. The medical device system of claim 8, wherein the location of the display device is a global positioning system location.

10. The medical device system of claim 1, wherein the at least one processor is further configured to
    make a determination that the first defibrillator has moved outside the range of the transceiver based on a changed first device signal; and
    in response to making the determination, provide an indication that the first defibrillator is missing.

11. A method of determining locations of medical devices, the method comprising:
    sensing a presence of a first defibrillator within a range of a transceiver based on the transceiver wirelessly receiving a first device signal generated by the first defibrillator, the first device signal having a first signal strength;
    receiving a second device signal from a second defibrillator via the transceiver;
    measuring a second signal strength of the second device signal;
    estimating a first distance between the first defibrillator and the transceiver based on the first signal strength;
    estimating a second distance between the second defibrillator and the transceiver based on the second signal strength;
    maintaining an active list of medical device inventory, the active list comprising information regarding the first defibrillator, the first distance, the second defibrillator, and the second distance;
    providing an indication of the estimated first distance between the first defibrillator and the transceiver and an indication of the estimated second distance between the second defibrillator and the transceiver via a display device; and providing an alert via the display device in response to sensing the presence of the first defibrillator within the range of the transceiver.

12. The method of claim 11, further comprising providing the indication of the estimated first distance and the estimated second distance to a mobile device in response to a request received from the mobile device.

13. The method of claim 12, further comprising providing navigation information associated with the first defibrillator and/or the second defibrillator to the mobile device.

14. The method of claim 11, further comprising:
making a determination that the first defibrillator has moved outside the range of the transceiver based on a changed first device signal; and
in response to making the determination, providing an indication that the first defibrillator is missing.

15. A method of determining locations of medical devices via a mobile device, the method comprising:
responding to a notification from a server using the mobile device, the notification indicating a need for one or more defibrillators;
receiving, at the mobile device from the server, location information for the one or more defibrillators; and
receiving, at the mobile device, navigation information to retrieve a closest defibrillator of the one or more defibrillators.

16. The method of claim 15, further comprising receiving, from the server, maintenance information associated with at least one of the one or more defibrillators.

17. The method of claim 15, further comprising transmitting, to the server, a confirmation of a location of any one of the one or more defibrillators.

18. The method of claim 15, further comprising transmitting, to the server, a picture of a global positioning system location of any one of the one or more defibrillators.

19. The method of claim 15, wherein the notification further indicates that a user has requested the one or more defibrillators.

20. The method of claim 15, further comprising receiving, at the mobile device from the server, location information for an alternative defibrillator of the one or more defibrillators.

21. The method of claim 15, further comprising receiving, at the mobile device from the server, location information for an alternative defibrillator of the one or more defibrillators, wherein the location information for the alternative defibrillator is received when the closest defibrillator has an outstanding service need.

22. The method of claim 15, further comprising receiving, at the mobile device from the server, notification of a maintenance need for at least one of the one or more defibrillators.

23. The method of claim 15, further comprising receiving, at the mobile device from the server, notification of a maintenance need for the closest defibrillator.

24. The method of claim 15, further comprising transmitting, to the server, a picture of an inventory location of any one of the one or more defibrillators.

25. The method of claim 15, wherein the mobile device has installed thereon a mobile application configured to provide guidance for performing cardiopulmonary resuscitation (CPR).

26. The method of claim 15, wherein the mobile device has installed thereon a mobile application configured to:
obtain treatment data from at least one of the one or more defibrillators; and
upload the treatment data to the server.

27. The method of claim 15, further comprising receiving, at the mobile device from the server, device information for at least one of the one or more defibrillators, wherein the device information includes at least one of device model information, device manufacturer information, or battery type information.

28. The medical device system of claim 15, wherein the mobile device is a smart watch, a smart phone, or a tablet.

* * * * *